US006306176B1

(12) United States Patent
Whitbourne

(10) Patent No.: US 6,306,176 B1
(45) Date of Patent: *Oct. 23, 2001

(54) BONDING LAYERS FOR MEDICAL DEVICE SURFACE COATINGS

(75) Inventor: Richard J. Whitbourne, Fairport, NY (US)

(73) Assignee: STS Biopolymers, Inc., Henrietta, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/400,867

(22) Filed: Sep. 21, 1999

Related U.S. Application Data

(63) Continuation-in-part of application No. 08/791,440, filed on Jan. 27, 1997, now Pat. No. 5,997,517.

(51) Int. Cl.$^7$ .................................................. A61F 2/28
(52) U.S. Cl. .................... 623/23.59; 623/1.46; 427/2.24; 523/113
(58) Field of Search ............................... 623/1.46, 23.59; 604/265; 427/2.24; 523/113

(56) References Cited

U.S. PATENT DOCUMENTS

| | | |
|---|---|---|
| 3,695,921 | 10/1972 | Shepherd et al. |
| 3,939,049 | 2/1976 | Ratner et al. ................... 204/159.13 |
| 4,055,682 | 10/1977 | Merrill ................................... 427/2 |
| 4,087,567 | 5/1978 | Sullivan ................................. 427/2 |
| 4,100,309 | 7/1978 | Micklus et al. ........................ 427/2 |
| 4,119,094 | 10/1978 | Micklus et al. ..................... 128/132 |
| 4,143,423 | 3/1979 | Sternlieb ................................ 2/168 |
| 4,330,956 | 5/1982 | McCarthy ................................. 43/4 |
| 4,361,626 | 11/1982 | Boba et al. .......................... 428/420 |
| 4,373,009 | 2/1983 | Winn .................................. 428/424.2 |
| 4,381,008 | 4/1983 | Thomas et al. ...................... 604/265 |
| 4,401,124 | 8/1983 | Guess et al. ........................ 128/1604 |
| 4,459,317 | 7/1984 | Lambert ................................... 427/2 |
| 4,459,318 | 7/1984 | Hyans ................................... 427/36 |
| 4,482,577 | 11/1984 | Goldstein et al. ...................... 427/2 |
| 4,534,363 | 8/1985 | Gold ................................... 128/772 |
| 4,557,724 | 12/1985 | Gregonis et al. ..................... 604/49 |
| 4,585,666 | 4/1986 | Lambert ................................... 427/2 |
| 4,589,873 | 5/1986 | Schwartz et al. .................... 604/265 |
| 4,642,267 | 2/1987 | Creasy et al. ....................... 428/413 |
| 4,678,660 | 7/1987 | McGary et al. ....................... 424/25 |
| 4,729,914 | 3/1988 | Kliment et al. ....................... 428/36 |
| 4,758,475 | 7/1988 | Eckes et al. ....................... 428/423.1 |
| 4,769,013 | 9/1988 | Lorenz et al. ....................... 604/265 |
| 4,773,901 | 9/1988 | Norton ................................. 604/265 |
| 4,781,703 | 11/1988 | Walker et al. ....................... 604/264 |
| 4,835,003 | 5/1989 | Becker et al. ........................... 427/2 |
| 4,847,324 | 7/1989 | Creasy ................................... 525/57 |
| 4,867,174 | 9/1989 | Skribiski ............................. 128/772 |
| 4,872,867 | 10/1989 | Joh ...................................... 604/269 |
| 4,876,126 | 10/1989 | Takemura et al. .................. 428/35.7 |
| 4,879,135 | 11/1989 | Greco et al. ............................ 427/2 |
| 4,883,699 | 11/1989 | Aniuk et al. ........................ 428/36.9 |
| 4,884,579 | 12/1989 | Engelson ............................. 128/772 |
| 4,906,237 | 3/1990 | Johansson et al. .................. 604/265 |
| 4,950,257 | 8/1990 | Hibbs et al. ......................... 604/265 |

(List continued on next page.)

FOREIGN PATENT DOCUMENTS

| | | |
|---|---|---|
| 0 184 465 | 6/1986 | (EP) . |
| 0 328 421 | 8/1989 | (EP) . |
| 0 379 156 | 7/1990 | (EP) . |
| 0 380 102 | 8/1990 | (EP) . |
| 0 407 965 | 1/1991 | (EP) . |

(List continued on next page.)

OTHER PUBLICATIONS

Klempner, D., "Interpenetrating Polymer Networks," Angew. Chem. Int. Engl. 17.97–106, 1978 (no month).

Lorenz, D.H., "The Use of Hydromer Coatings on Medical Devices," Medical Plastics Technology Seminar, Ann Arbor, Michigan, Hydromer, Inc., Oct. 4, 1984.

Kirk–Othmer, "Concise Encyclopedia of Chemical Technology," John Wiley & Sons, pp. 24–26, 90–92, 431–433, 437–439, 814–818, 1115–1117, and 1225–1228, 1985 (no month).

"Acryloid Acrylic Resins for Industrial Finishing," Rohm and Haas, Sep. 1985.

Martinson, C.R., et al., "Surface Coatings," McGraw–Hill Encyclopedia of Science & Technology, 6th Edition, vol. 18, p.7, 1987 (no month).

EPOTUF® EPOXY RESIN Solution 38–505, Product Bulletin, Reichhold Chemicals, Inc., Nov. 1987.

Moore, et al., "Endovascular Surgery," W.B. Saunders Company, pp. 157–159, 1989 (no month).

Kroschwitz, J.I., Concise Encyclopedia of Polymer Science and Engineering, John Wiley & Sons, pp. 15–20, 47–48, 344–349, 350–351, 458–459, 716–719, 1119, 1140–1141, 1230–1232, and 1264–1272, 1990 (no month).

(List continued on next page.)

Primary Examiner—Michael J. Milano
Assistant Examiner—Choon Koh
(74) Attorney, Agent, or Firm—Venable; Michael A. Gollin

(57) ABSTRACT

The medical device is coated with a thin coherent bond coat of acrylics, epoxies, acetals, ethylene copolymers, vinyl polymers containing hydroxyl, amine, carboxyl, amide or other reactive groups, and copolymers thereof. Outer layers may be applied and remain adherent to the substrate in water for an extended period. The bond coat may comprise cross linkers such as urea resins, melamines, isocyanates, and phenolics. Preferred polymers include vinylpyrrolidone-vinyl acetate, styrene acrylic polymer, ethylene acrylic acid copolymer, carboxyl function acrylic polymer, hydroxyl function acrylic polymer, and acrylic dispersion polymer. The coatings may be applied to inert metal or plastic surfaces of medical devices such as needles, guide wires, catheters, surgical instruments, equipment for endoscopy, wires, stents, angioplasty balloons, wound drains, arteriovenous shunts, gastroenteric tubes, urethral inserts, laparoscopic equipment, pellets, and implants. Methods of coating and coating liquids are provided.

27 Claims, No Drawings

U.S. PATENT DOCUMENTS

| | | | |
|---|---|---|---|
| 4,959,074 | 9/1990 | Halpern et al. | 623/66 |
| 4,977,901 | 12/1990 | Ofstead | 128/772 |
| 4,990,357 | 2/1991 | Karakelle et al. | 427/2 |
| 4,991,602 | 2/1991 | Amplatz et al. | 128/772 |
| 5,013,717 | 5/1991 | Solomon et al. | 514/56 |
| 5,041,100 | 8/1991 | Rowland et al. | 604/265 |
| 5,047,045 | 9/1991 | Arney et al. | 606/194 |
| 5,061,254 | 10/1991 | Karakelle et al. | 604/265 |
| 5,069,226 | 12/1991 | Yamauchi et al. | 128/772 |
| 5,084,315 | 1/1992 | Karimi et al. | 428/36.6 |
| 5,088,125 | 2/1992 | Ansell et al. | 2/167 |
| 5,129,890 | 7/1992 | Bates et al. | 604/281 |
| 5,160,790 | 11/1992 | Elton | 428/412 |
| 5,331,027 | 7/1994 | Whitbourne | 524/37 |
| 5,416,131 | 5/1995 | Wolff et al. | 523/105 |
| 5,429,839 | 7/1995 | Graiver et al. | 427/155 |
| 5,443,907 | 8/1995 | Slaikeu et al. | 428/375 |
| 5,452,726 | 9/1995 | Burmeister et al. | 128/772 |
| 5,523,095 | 6/1996 | Wilson et al. | 424/486 |
| 5,525,348 | 6/1996 | Whitbourne et al. | 424/423 |
| 5,662,960 | 9/1997 | Hostettler et al. | 427/2.3 |
| 5,670,558 | 9/1997 | Onishi et al. | 523/112 |
| 5,824,048 | 10/1998 | Tuch | 623/1 |
| 5,853,745 | 12/1998 | Darouiche | 424/423 |
| 5,997,517 | 12/1999 | Whitbourne | 604/265 |

FOREIGN PATENT DOCUMENTS

| | | |
|---|---|---|
| 2 064 556 | 6/1981 | (GB) . |
| 89/09626 | 10/1989 | (WO) . |
| 90/05162 | 5/1990 | (WO) . |
| 94/16747 | 8/1994 | (WO) . |
| 98/58690 | 12/1998 | (WO) . |

OTHER PUBLICATIONS

Stevens, M.P., "Polymer Chemistry: An Introduction," $2^{nd}$ Ed., Oxford University Press, 1990 (no month).

"AROLON ® 820–W–49 Vehicle for Water Thinned Industrial Maintenance Finishes," Product Bulletin, Reichhold Chemicals, Inc., Mar. 1993.

"EPOTUF ® 37–618 Polyamide Solution," Product Bulletin, Reichhold Chemicals, Inc., Mar. 1993.

"CYMEL ® 303 Crosslinking Agent," CYTEC Industries Inc., 1995 (no month).

"RHOPLEX ® B–15J Heat–Sealable, Acrylic Binder for Nonwovens," Rohm and Haas, 1995.

BONDING LAYERS FOR MEDICAL DEVICE SURFACE COATINGS

This is a Continuation-in-Part of U.S. patent application Ser. No. 08/791,440 filed Jan. 27, 1997, now U.S. Pat. No. 5,997,517 which is incorporated herein by reference in its entirety.

BACKGROUND OF THE INVENTION

1. Field of the Invention

The present invention relates to an adhesive coating for a medical instrument. More specifically, the invention relates to polymer compositions which, when applied to an insertable medical device, provide for improved adhesion of a coating to the surface of the device, and related methods.

2. Related Art

Medical devices such as catheters or guide wires are inserted through trachea, blood vessels, urethra or other celoms or tissues, or through catheters or drainage tubes etc. Such devices are required to have a high degree of smoothness to assure introduction of such devices without causing trauma to tissue encountered during placement. These surfaces may be further enhanced by having lubricity for preventing injury or inflammation of mucous membrane which would be caused when the devices remain in the tissue. Other requirements for medical device surfaces have also been recognized.

In some instances, it is advantageous for medical device surfaces to have the capability of serving as a depot for various physiologically active substances such as anti-thrombogenic substances, anti-microbial substances, anti-neoplastic substances, genetic materials, hormones, living cellular materials and others. Anti-thrombogenic materials, such as complexes of heparin with quaternary ammonium compounds, are used on medical device surfaces to prevent formation of blood clots on the surface, which can form rapidly on vascular prostheses in vitro. Antimicrobial agents including penicillins, cephalosporins, fluoroquinolones, aminoglycocides, silver, compounds, phenol compounds, biguanides and others have been proposed for use in surface coatings to control nosocomial infections that often occur on surfaces of implanted prostheses, U.S. Pat. Nos. 5,069,899, 5,525,348, and 4,442,133.

The construction of devices such as guide wires and catheters presents special problems for insertion. Guide wires generally include coiled guide wires formed of stainless steel and monofilament guide which may have plastic materials such as polyurethanes, polyamides, polyolefins, etc. extruded over them to provide a surface to which coatings can adhere, and to provide smoothness and uniformity of the surface.

Catheters typically consist of plastic tubes which may have a single lumen or multiple lumens. Catheters may have balloons fastened along the tube to obstruct a vessel or to fix the catheters in a desired position. Catheters may also have ports at the distal end, side ports along part of the length, or other mechanical features needed to accomplish the particular device mission. Catheters may consist of a continuous length of tubing, or may comprise two or more sections of tubing consisting of similar or dissimilar materials which are welded together in order to have different properties at different locations along the length of the device. Catheters may be tapered, both within a segment or by having segments of differing diameters. Typical material of which catheters are constructed include polyamides, polyurethanes, vinyls such as polyvinylchloride, polyesters, polyolefins, silicones, and others. Typical diameters range from less than one millimeter to more than 8 millimeters.

As typically encountered in inserting a catheter, at the predetermined site, the guide wire tip is inserted through a catheter up to its tip opening, the catheter with the guide wire is inserted into for example a blood vessel percutaneously, and the catheter is further inserted through the vessel by using the guide wire as a leading and supporting guide. These operations produce friction and abrasive forces that apply to the surfaces of the medical device. It is desirable for the frictional resistance between the catheter inner surface and the guide wire to be low. Relatively high friction between the catheter and the guide wire not only prevents the guide wire from being inserted through the catheter, but the guide wire from being easily moved through the catheter, making it difficult to carry out subtle indwelling operations at the destined vessel site. Sometimes the guide wire cannot be withdrawn from the catheter, rendering the catheter lumen unusable despite the completion of the indwelling operation.

To avoid such problems, attempts have been made in the prior art to apply low frictional resistance Teflon and silicone oil to the outer surface of guide wires. Application of silicone oil fails to retain lubricity because of immediate loss of silicone coatings. Frequent applications add to frictional resistance, also undesirably creating troubles as mentioned above.

There is thus the need for a catheter and guide wire having a lower frictional resistance surface which enables more subtle operation in a vessel and can be easily inserted and remain at the site where catheters are otherwise difficult to manage during placement.

Polyurethane coatings have been applied directly on metal surfaces. U.S. Pat. No. 4,876,126. However, commercial versions of this technology require thick layers (60–80 microns thick) in order to perform adequately. In practice, the thick layer extends continuously around the coated metal substrate. These layers have good cohesive forces and thus appear to be tightly bound on the metal surface, even though these layers do not necessarily have good adhesion to the metal surface. A disadvantage of such coatings is that because the polyurethane and other plastic layers are so thick, the metal diameter of the underlying wire must be correspondingly diminished. This is especially troublesome on the very fine wires such as those used in coronary angioplasty or neurointerventional catheterization procedures. These wires have OD's of about 0.010"(about 250 microns) and may have the majority of the diameter (about 120 to 170 microns) composed of plastic materials instead of metals. An alternate method is the use of low frictional materials such as polytetrafluoroethylene coatings which have lower friction than metals and most other plastic materials and which can be applied directly onto metallic substrates. Other materials such as high density polyethylene have been tried, but the coefficients of friction are not low enough for such materials. Oils have been applied, and the coefficients of friction are low. However, such treatments are transient because they wear off during use.

Hydrogel coatings are known to provide a lubricious surface for insertable devices. However, metals and certain plastic materials such as polyolefins, polyamides, silicones, polyesters and some others have inert surfaces and it is often difficult to achieve acceptable adhesion when applying surface coatings, including hydrogel coatings, over such surfaces.

Hydrogels can absorb several times their weight in water when placed in an aqueous environment. Usually, hydrogel layers are attached to hydrophobic sublayer(s) and there may be a great deal of penetration of the hydrogel polymer molecules into the hydrophobic sublayer(s). The polymer molecules of both layers are left in a state of inter-molecular mingling, especially in the region of the interface between the two layers. As a result of the inter-molecular mingling, water that is taken up in the hydrogel may find its way to the intersection between the substrate and the hydrophobic coating layer. The adhesion between the hydrophobic layer and the substrate is usually jeopardized by the moisture, and adhesive failure usually results. This process of moisture-induced adhesive failure is greatly exacerbated when the coating layers are thin.

Thin hydrophobic layers containing cellulose esters and acrylic polymers may be coated directly on metal substrates, U.S. Pat. No. 5,001,009. Hydrogel coatings may be applied directly over such layers. Such systems perform well on coil type guide wires, because the coating is able to gain additional adhesion by penetrating between the coil wires. However, such layers tend to allow too much moisture penetration resulting in deterioration of adhesive bonds when applied onto mandril style metal substrates.

SUMMARY OF THE INVENTION

It is an object of the present invention to provide materials which can be applied within layers directly on medical device surfaces on which it is difficult to achieve coating adhesion, and which allow layers to be applied over them to enhance performance and biocompatibility of such devices. It is another object of the present invention to provide methods for preparing such medical instruments.

It is a further object of the present invention to provide guide wires, catheters, drainage tubes, feeding tubes, and other devices which are used in contact with human tissues and fluids, with surfaces that show enhanced biocompatability and may become very lubricious when contacted by body fluids. It is another object to provide such devices which contain substances which combat infections, blood clots, inflammation, and other disorders that may result from in vitro placement and use of such medical devices.

According to a first aspect of the present invention, there is provided a medical device comprising a substrate having a surface to be coated. The surface is characterized as being relatively inert and does not have reactive functional groups on the surface. A polymer coating which may be a single or mixed (hybrid) polymer layer is provided on the substrate surface which is strongly bonded to the substrate surface. The polymer layer on the device surface is such that other layers applied over it will be strongly bonded to such layer.

Substrates to which coatings according to the invention may be applied include metals such as stainless steel, nickel, gold, chrome, nickel titanium alloy, platinum and others; plastics such as silicone, polyethylene, other polyolefins, polyesters, and others. Preferred devices include needles, guide wires, catheters, surgical instruments, equipment for endoscopy, wires, stents, angioplasty balloons, wound drains, arteriovenous shunts, gastroenteric tubes, urethral inserts, laparoscopic equipment, pellets, or implants. Particularly preferred embodiments include coated guide wires, particularly mandrel-type wires, catheters, drainage tubes, insulation in pacemaker leads, and smooth thin wires for coronary angioplasty or neurointervention or other procedures requiring a wire thickness of less than about 10–20 mils (250–500 microns).

According to a second aspect of the present invention, there are provided methods for preparing medical devices, comprising coating the medical device surface with a thin polymer layer of suitable composition such that the thin layer bonds well to the substrate surface, and such that succeeding coated layers will be strongly bonded to said thin polymer layer. The device is then coated with other layers designed to enhance performance and for biocompatibility of the medical device. Such layers may include medicated coatings which can serve as surface reservoirs for physiologically active agents to release efficacious concentrations of such agents near the device surface, hydrogel coatings to provide surface lubricity, color containing coatings, abrasion resistant coatings, combinations of one or more of the above, and other coatings intended to enhance the performance of the device.

This invention satisfies a long felt need for a thin well-bonded lubricious coating for indwelling medical devices. The invention succeeds where previous efforts at bonding surface layers to medical devices have failed, despite extensive efforts in a crowded and mature art. The invention eliminates the need for thick coatings, with enhanced performance. The materials and methods of the invention were not previously known or suggested, and their advantages were not previously appreciated. Further objectives and advantages that can be attained by the present invention will become apparent from the detailed description.

DETAILED DESCRIPTION OF THE PREFERRED EMBODIMENTS

In describing preferred embodiments of the present invention, specific terminology is employed for the sake of clarity. However, the invention is not intended to be limited to the specific terminology so selected, and it is to be understood that each specific element includes all technical equivalents which operate in a similar manner to accomplish a similar purpose.

Thin bond or tie coat layers according to the invention may be applied to difficult-to-bond-to substrates in order that other layers which cannot normally be bonded to such substrates may be satisfactorily bonded. The polymers of the invention are sufficiently resistant to degradation by solvents in succeeding layers that the coating does not lose adhesiveness when soaked in water and is impervious to water diffusion from the surface.

Classes of polymers which may be employed include acrylic polymers and copolymers based on monomers such as methylmethacrylate, butylmethacrylate, isobutylmethacrylate, ethylmethacrylate, methylacrylate, acrylic acid, styrene methacrylate, styrene acrylate, and others; vinyl polymers and copolymers such as polyvinylpyrrolidone, vinylpyrrolidone-vinylacetate copolymers, ethylene acrylic acid copolymers, epoxy polymers, and others. Exemplary commercial products that may be used in the invention include acrylics such as ARYLOID$^R$ (Rohm & Haas) AT-63, AT-51, AT-81, WR-97; Polyvinylpyrrolidone polyvinyl acetate copolymers such as PVP/VA (GAF) E-335, E-635; ethylene acrylic acid copolymers such as PRIMACOR™ (DOW) 5989, 5990; melamine resins such as CYMEL (CYTEC Industries) 303, 370, 380; epoxies such as EPON (Shell) 1001. Other appropriate polymers having the requisite characteristics will be apparent to persons of ordinary skill.

The polymers preferably, but not necessarily, contain reactive groups or points of reactivity such as hydroxyls, mono-, di- and tertiary amines, acids such as carboxyl, amides, or other groups which represent points of chemical reactivity. The polymers and points of chemical reactivity are able to form attractive forces such as hydrogen bonding toward the medical device surface, and also toward the coating layers to be applied over them. Such bonds are very strong, and prevent penetration of the top coat layer and water without requiring covalent or other ionic links between the device surfaces and the thin polymer tie coatings.

Polymers with reactive groups are preferred to help bond with substrates like metals. However, polymers lacking such groups such as acrylic or styrene polymers may also be used.

The reactive groups can also react to form a cross-linked matrix or help to form a cross-linked matrix. If desired, cross-linkers such as urea resins, melamines, isocyanates, phenolics, and others may be incorporated to cross-link the polymers of the invention with themselves, by reacting with the points of chemical reactivity on the polymer chains. Alternatively, cross-linkers may react with themselves to form a cross-linked matrix in which the tie coat polymers are enmeshed, resulting in a solvent-resistant layer. Cross-linking within the thin polymeric tie coats (either between the principal polymers or around them) is useful in promoting effective adhesion by ensuring that the solvents used in succeeding coating layers do not attack and degrade the tie coat polymer layer excessively and by resisting water penetration. When the tic coat layers are subjected to excessive solvent attack the polymer tie coat layer may be diluted by the succeeding coating layer thereby degrading the adhesive bond between the tie coat layer and the medical device surface. Excessive water penetration can also degrade adhesion.

Coatings according to the invention may be prepared with polymers that lack points of reactivity, such as acrylic or styrene polymers or copolymers. Likewise, coatings may be made without cross-linking. However, with such coatings a greater tie coat thickness may be required or desirable than with layers made of polymers with points of reactivity and layers with cross-linking, in order to achieve a high degree of adhesion of succeeding layers according to the invention. For example, cross-linked coatings with polymers having reactive groups may be about two to about ten microns thick, in contrast with a coating as in Example 1, where a water-borne acrylic styrene copolymer is applied to metal, with a hydrogel layer on top, and a total thickness of about 30–40 microns.

The tie coat layers of the present invention are extremely durable, even when immersed in water for prolonged periods. As will be shown in examples, coatings on stainless steel can be soaked in water for months without losing adhesion, even when hydrogel layers are applied to the samples. Hydrogel layers typically absorb several times their weight in water and serve as a pathway for water diffusion into the layer (s) between the hydrogel layer and the medical device surface. Such exposure to water, especially for extended periods represents a considerable challenge to the tie coats of the present invention and the fact that they are able to endure such challenges without adhesive failure is a surprising result. The tie coat layers of the present invention are so thin, typically less than 5 microns, that the adhesiveness is all the more remarkable.

The coatings of the invention may be thin, on the order of 0.0002"–0.0005" (5–12 microns), although it may be as thick as is desirable. Preferably, the coating is in the range of about 2 to about 100 microns, more preferably less than about 80 microns, or 60 microns, and particularly preferred embodiments are less than about 15 microns thick. Bond coats of about 2 to about 10 microns are generally quite adequate. If the coating is thicker, it may cause other problems in certain applications where thinness is important.

A coating according to the invention may include a bond coat of about 5 microns and a two-layer hydrogel comprising a 5 micron base coat and a 5 micron top coat, with a total thickness of about 15 microns.

Examples of substrates and bond coat formulations that are effective with them are listed below. Many other combinations will be apparent to a person of ordinary skill following the teachings of the invention.

| | |
|---|---|
| stainless steel: | epoxy resin; vinylpyrrolidone-vinyl acetate copolymer; styrene acrylic aqueous dispersion; ethylene acrylic acid copolymer plus melamine resin; ethylene acrylic acid copolymer plus melamine resin plus hydroxyl function acrylic polymer plus isocyanate polymer; carboxyl function acrylic polymer plus epoxy resin; acrylic dispersion polymer |
| polyethylene | ethylene acrylic acid copolymer plus melamine resin plus hydroxyl function acrylic polymer plus isocyanate polymer |
| silicone | ethylene acrylic acid copolymer plus melamine resin plus hydroxyl function acrylic polymer plus isocyanate polymer plus oxygen plasma |
| polyester | ethylene acrylic acid copolymer plus melamine resin plus hydroxyl function acrylic polymer plus isocyanate polymer |
| polyamide | oxygen plasma plus polyvinylbutynal |

The coatings are coherent in that they form a continuous surface layer. When coated with a top coat, the resulting coatings are resistant to removal on prolonged soaking in aqueous fluids, and are adherent to a wide variety of substrates.

There are several useful tests of adhesion of coatings comprising the bond coat of the invention. Two of them are the dry adhesion tape test and the wet rub test. Uncovered tie coat coatings generally adhere well to a substrate, as do tie coat coatings with a base coat such as a cellulose ester layer, but problems frequently arise when a surface coating is applied, such as a hydrogel. Completed coatings according to the invention are able to endure immersion in water for at least an hour and remain adhesive and resistant to removal by abrasion as indicated by the wet rub test, and, after drying, the tape test. This sets them apart from the prior art.

In the wet rub test, parallel cuts are made through the coating with a razor or knife. The coating is immersed in water for a predetermined period, such as an hour. A finger is then rubbed briskly across the cuts. Peel-back of the coating constitutes coating failure. In the dry adhesion test, adhesive tape is pressed firmly onto the coating, then peeled off briskly. Removal of the coating constitutes failure.

The coatings according to the invention may be applied to the surface of a biomedical device or other device with sufficient thickness and permanence to retain the coating's desirable qualities throughout the useful life of the coated device. They have sufficient thinness to be useful in many applications inappropriate for prior art coatings. The coatings of the invention are nonreactive with living tissue and are non-thrombogenic in blood.

The coatings may be applied by various techniques such as dip, spray, brush, wipe, or other methods known to those skilled in the art. The coating solutions have low viscosities, typically less than 100 CPS, and have good spreading properties. The coatings are baked at elevated temperatures, typically 50° C. to 100° C., to drive off the organic solvents.

Gas plasma treatment may be done according to conventional methods. A vacuum is drawn, a gas such as oxygen or ammonia is allowed in, it is excited with Rf, and the surface is allowed to stay in contact with the resulting plasma for a sufficient time, such as 20 minutes, to put functional groups on the surface. Oxygen produces hydroxyl surface groups, and ammonia produces amine groups covalently bound to the polymer surface. Over time the groups tend to fold into the surface and become less reactive, so plasma-treated surfaces are best used fresh.

The coating systems described herein produce coatings that remain bonded in aqueous fluids on surfaces such as polyethylene, polypropylene, polyamide, polyester, silicone and metals such as stainless steel, platinum, gold, nickel, titanium, nickel-titanium alloys, chrome and other surfaces that are generally considered as presenting adherence problems. It may be necessary to treat some surfaces with gas plasma or other ionizing treatment to promote adhesion to the substrates. The following examples show some embodiments of how the invention can be used.

The coatings of the present invention are designed to remain coherent and adhesive under torturous conditions. In one embodiment, a guide catheter is inserted into a femoral artery at the leg up to the aortic arch. This is a fairly straight and direct route. Into the guide catheter, a guide wire is inserted. A device catheter is then inserted into the guide catheter and over the guide wire. The device catheter may be used for, for example, angioplasty, stenting, drug delivery aneurysm repair or other purposes. The device catheter typically has a gradual curve at the last about 1 cm of the end being inserted over the guide wire and may generate a great deal of abrasion between the guide wire and the device catheter during use as described below.

The device catheter and guide wire are then further inserted into the vasculature beyond the end of the guide catheter at the aortic arch and into the cardiac arteries or the brain. In continuing into these further channels in the body, the guide wire and device catheter must be capable of traversing numerous low radius turns encountered in the vasculature. When a bifurcation is encountered in a vessel, the curvature at the tip of the device catheter is turned in the desired direction, directing the guide wire.

The guide wire and the device catheter are moved stepwise through the vasculature, i.e. the guide wire is inserted a short distance and then the device catheter is inserted over the guide wire. For example, the guide wire may be inserted 2 cm while holding the device catheter in place. The device catheter is then inserted over the guide wire while the guide wire is held in place. This produces even further abrasion between the guide wire and the device catheter. In addition, there is abrasion between the guide wire and tissue and between the device catheter and tissue.

As mentioned above, numerous turns may be encountered in the vasculature while inserting the catheter and guide wire. For example, there may be numerous turns on the order of 1–3 cm in diameter. In addition, there may be turns with a diameter of less than or equal to 1 cm. Under these extreme conditions, coatings present in the prior art fail by losing adhesion, losing lubricity or cracking. Such failure can be catastrophic in the intravascular environment (e.g. failure could cause an embolism) and must be avoided. Accordingly, the coatings of the invention remain adherent when subjected to bending through a small radius. Typically, a small radius means less than about 3 cm.

Unlike prior art coatings, the coatings of the present invention are able to withstand these extreme uses. Use of the present coatings on the guide wire, on the inside and/or outside of the device catheter and/or on the inside and outside of the guide catheter sufficiently prevent abrasion of the coatings while maintaining lubricity. This allows the catheters and guide wires to be inserted without damaging tissue, the guide wire or the catheter, even in demanding applications that require a great deal of bending of the device catheter and guide wire and that require repeated motion between the device catheter and guide wire.

In U.S. Pat. No. 5,620,738 to Fan et al., inventors at Union Carbide focused their disclosure on a particular class of copolymers that may be used with hydrophilic polymers to form lubricious coatings. The Fan et al. copolymers are formed of at least one vinyl moiety and at least one carboxylic acid moiety, in the same monomer or in different monomers of the copolymer. The vinyl monomer is preferably vinyl chloride or another vinyl halide and is present as a major component of the polymer. Having carboxylic acid moieties together with the vinyl moieties in copolymers is critical to the coatings described by Fan et al. The particular binder copolymers disclosed by Fan et al. each include a vinyl chloride monomer, or a vinyl acetate or butadiene monomer, copolymerized with maleic acid or acrylic acid. In contrast, in accordance with the present invention, there is no requirement for a copolymer of a vinyl monomer with a carboxylic acid monomer. In most of the examples in Fan et al., the substrate is polyvinylchloride, and the binding polymer is vinyl chloride, and it is preferred to have the same monomer in the binder as the substrate. For example, Fan et al. coated polyvinyl chloride tubes with vinyl ether-maleic anhydride copolymer and converted the anhydride to maleic acid. In other examples, a vinyl chloride-vinyl acetate-maleic acid copolymer was used to coat PVC tubes. Alternatively, the copolymer had -acrylate monomer instead of -maleic acid. However, PVC is easy to coat because it is susceptible to solvent attack, leading to an inter-penetrated surface.

Although Fan et al. mention substrates other than PVC, and have three examples applied to polyethylene tubes, the Fan et al. coatings are preferably penetrated into the substrate. This teaches away from use of such coatings on metals and inert non-penetrable surfaces. Indeed, in contrast with examples using PVC substrates, Fan et al. contains no statement that the coatings applied to polyethylene tubes were abrasion resistant, suggesting that the Fan et al. coating lacked the superior abrasion-resistance of the present invention. In contrast to coatings such as in Fan et al., the present invention is effective on inert substrates without the need for penetration. There may be some incidental or superficial penetration on certain polymer substrates, but not significant penetration as would be found, for example, with polyvinylchloride substrates. In this context, the phrase "not penetrated" embraces incidental or superficial penetration as will be understood by a person of skill in the art. Thus, the benefits of the invention are met without penetration, but the presence of some penetration does not eliminate the advantages of the invention.

The coatings of Fan et al. may be applied as a one step or two step coating, and Fan et al. does not distinguish in the end result arising from use of one or the other approach. In contrast, with the present coatings, the outer layer is applied to the bond coat layer. This permits the bonding polymer components to bond to the substrate and to each other before application of the surface coating material. Fan et al. teach away from selecting a two step process in which the bonding layer is formed first.

Fan et al. do not teach any coating that would adhere to stainless steel, silicone, polyamide, or nylon, in contrast to the claimed invention here, which achieves that extremely difficult standard. The composite coatings of the present invention achieve unexpectedly superior performance on such substrates.

Prior art coatings comprising non-cross linked chlorinated polyolefins suffer from other disadvantages. For example, such coatings do not adequately bond to metals. In addition, if plasma pretreatment of substrates is used, polyolefin coatings must be applied within 24 hours of pretreatment to prevent failure of the coatings. In contrast, the coatings of the present invention may be applied more than 24 hours after pretreatment, and the coatings of the present invention are sufficiently adhesive to metals to withstand the severe abrasion and numerous turns of the vasculature which may be encountered in use.

The present invention is an improvement over coatings such as chlorinated polyolefin coatings on polyethylene tubing. The present coatings have unexpectedly superior adhesion and abrasion resistance as compared to the prior art coatings. Thus, while the prior art chlorinated polyolefin coating is suitable for less stringent applications such as on polyurethanes and polyesters that do not require high specific adhesion, the improved coatings of the present invention allow for use in a much broader range of applications. These additional applications include use on substrates such as metals, including nickel titanium alloy, nickel, gold, chrome, platinum and stainless steel, and plastics, including polyolefins such as polyethylene and polypropylene, silicones, latex rubbers, polyisocyanates, and others, for which the prior art coatings are not sufficiently adherent nor sufficiently abrasion resistant.

EXAMPLE 1

A stainless steel surface was brush coated with the following solution, and dried for 30 minutes at 85° C. Add in order, stir until dissolved.

| | |
|---|---|
| Epoxy resin | 5.55 gm |
| Xylene | 2.37 gm |
| Tetrahydrofuran (THF) | 62.08 gm |
| Cyclohexanone | 10.0 gm |
| Ethanol | 2.5 gm |
| Vinylpyrrolidone-vinylacetate copolymer | 2.5 gm |

The coating was tested for adhesion by cutting lines through it with a knife and then rubbing briskly across the cuts with a finger after the coating was immersed in water. No failure of adhesion (i.e. peel back) occurred after the wet rub test. Next, the coating dry adhesion was tested by pressing Universal Tape 83436 tape (United Stationers Supply, Co.) firmly onto the coating and peeling the tape off briskly. No coating should be removed by this test. This sample showed no adhesion failure on the tape test.

EXAMPLE 2

A styrene acrylic aqueous dispersion polymer (55% solids) was brush coated on a stainless steel surface, and dried for 30 minutes at 85° C. This coating showed excellent adhesion when tested according to example 1.

EXAMPLE 3

A sample as per example 2 was overcoated with a hydrogel composition consisting of:

| | |
|---|---|
| Polyvinyl pyrrolidone (PVP) | 9.4 gm |
| Ethanol | 136.1 gm |
| Butyrolactone | 30.6 gm |
| 0.0625% nitrocellulose in cyclohexanone | 3.8 gm |

The coating was dried for 25 hours at 85° C. The coating passed the wet and dry adhesion tests according to example 1.

EXAMPLE 4

The following solution was brush coated on a stainless steel surface, and dried at 85° C. for 2 hours.

| | |
|---|---|
| 5% (w/w) Ethylene acrylic acid copolymer in tetrahydrofuran (THF) | 15 gm |
| Cyclohexanone | 2 gm |
| Melamine resin | .24 gm |
| Xylene | .23 gm |
| Butanol | .07 gm |
| Trichloroacetic acid | .1 gm |

This coating was dried for 15 hours at 85° C. The adhesion of the coating was tested according to example 1, and had good adhesion under both wet and dry conditions.

EXAMPLE 5

A sample as per example 4 was overcoated with the following solution and dried 2 hours at 85° C.

| | |
|---|---|
| Nitrocellulose solution* | 170.6 gm |
| Cyclohexanone | 88.0 gm |
| Benzyl alcohol | 48.0 gm |
| 10% (w/w) polyurethane in THF | 86.0 gm |
| Acrylic polymer with hydroxyl function | 18.0 gm |
| Melamine resin | 4.5 gm |
| Xylene | 17.55 gm |
| Butanol | 4.95 gm |
| Trichloracetic acid | 0.5 gm |

*Nitrocellulose solution:

| | |
|---|---|
| ¼" RS Nitrocellulose | 687 gm |
| Butyl acetate | 459 gm |
| Toluene | 360 gm |
| Ethyl acetate | 894 gm |
| Camphor | 132 gm |
| Dibutylphthalate | 180 gm |

Next the sample was overcoated with the following hydrogel solution and dried for four hours at 85° C.

| | |
|---|---|
| PVP | 9.4 gm |
| Ethanol | 136.1 gm |
| Butyrolactone | 30.6 gm |
| 0.0625% Nitrocellulose solution in cyclohexanone | 3.8 gm |

The adhesion of the coatings was tested according to example 1 and had good adhesion under both wet and dry conditions. The sample had good wet lubricity. If the first coating was omitted the adhesion failed under the test condition.

EXAMPLE 6

The following solution wag dip coated on a stainless steel wire and dried for 2 hours at 85° C.

| | |
|---|---|
| 5% (w/w) ethylene acrylic acid copolymer in THF | 15 gm |
| Cyclohexanone | 4 gm |
| Hydroxyl function acrylic polymer | .24 gm |
| Melamine resin | .06 gm |
| 80% (w/w) isocyanate polymer in THF | .32 gm |
| Trichloroacetic acid | .20 gm |

Next the sample was overcoated with the same two overcoating solutions per example 5. The adhesion was good when tested according to example 1 under wet and dry conditions. The sample continued to show good adhesion after soaking in water for more than 130 days. The coating had good wet lubricity.

EXAMPLE 7

Polyethylene tubing was exposed to oxygen plasma treatment. The PE tube was then coated with the same coatings as per example 6. The adhesion was good when tested according to example 1 under wet and dry conditions. The sample had good wet lubricity.

EXAMPLE 8

Polyethylene tubing was treated as in example 7, except that the middle coating just underneath the hydrogel consisted of:

| | |
|---|---|
| ¼" RS Nitrocellulose | 2.89 gm |
| Dibutylphthalate | 1.1 gm |
| Camphor | .8 gm |
| Polyurethane | 6.8 gm |
| Cyclohexanone | 28.3 gm |
| Methylethylketone | 1.6 gm |
| Benzyl alcohol | 7.1 gm |
| THF | 10.1 gm |
| Ethylacetate | 2.3 gm |
| Ethanol | 14.7 gm |
| Isopropanol | 5.5 gm |
| Toluene | 22.9 gm |
| Butylacetate | 1.3 gm |

The sample had good adhesion when tested according to example 1 under both wet and dry conditions, and had good wet lubricity.

EXAMPLE 9

Silicone tubing was treated as in example 8. The coating had good adhesion when tested according to example 1 under wet and dry conditions, and the coating had good wet lubricity.

EXAMPLE 10

Silicone tubing was exposed to oxygen plasma treatment by placing in an evacuated vessel and subjecting to alternate cycles of adding oxygen and cycling Rf power. Initially, oxygen is fed in at 550±50 mTorr for 0.25 minutes. The oxygen is turned off, and the Rf power is turned on, with 450±50 watts forward and ≦50 watts reverse, for 2 minutes. These two steps are repeated five times, with the remaining oxygen cycles lasting 2 minutes. The tie coat is typically applied to the plasma treated surface before degradation of the plasma treatment, within a day or two.

Next, the treated tubing was dip coated with the following solutions and dried one hour at 85° C.

| | |
|---|---|
| Polyvinylbutyral | 18.0 gm |
| Ethanol | 35.4 gm |
| Xylene | 34.9 gm |
| Methylethyl ketone | 43.4 gm |
| Propylene glycol methyl ether acetate | 48.9 gm |
| Dipropylene glycol methyl ether acetate | 9.0 gm |
| Isobutyl acetate | 1.89 gm |

This coating was overcoated with the same hydrogel as used in example 3. The coated sample had good adhesion when tested according to example 1 under both wet and dry conditions, and had good wet lubricity.

EXAMPLE 11

Stainless steel was coated with the following solution and dried 60 minutes at 85° C.

| | |
|---|---|
| Polyvinyl butyral | 9.00 gm |
| Ethanol | 17.70 gm |
| Xylene | 18.19 gm |
| Methylethylketone | 21.70 gm |
| Propylene glycol methyl ether acetate | 24.45 gm |
| Dipropylene glycol methyl ether acetate | 4.50 gm |
| Isobutyl acetate | .90 gm |
| Acrylic polymer with hydroxyl function | 1.52 gm |
| Melamine resin | .38 gm |
| Butanol | .42 gm |

Next, the sample was overcoated with the last two coatings that were used to overcoat the first coating in example 5. The sample had good adhesion when tested according to example 1 under wet and dry conditions, and the sample had good lubricity.

EXAMPLE 12

A sample of polyester tubing was treated as per example 8. The sample had good adhesion when tested according to example 1 under wet and dry conditions, and the sample had good wet lubricity.

EXAMPLE 13

A stainless steel surface was dip coated with the following tie coat solution and dried 2 hours at 85° C.

| | |
|---|---|
| Carboxyl function acrylic polymer | 1.85 gm |
| Aromatic 150 | 2.32 gm |
| Butyl Cellosolve | .33 gm |
| THF | 3.55 gm |
| Xylene | .13 gm |
| Epoxy resin | .39 gm |

Next, the sample was overcoated with the same hydrogel coating as per example 3, and dried for 2 hours at 85° C. The sample had good adhesion when tested according to example 1 under wet and dry conditions, and had good lubricity.

EXAMPLE 14

A sample of stainless steel was dip coated with the same tie coat solution as used in example 1, and was then dried for 2 hours at 85° C. Next, the sample was overcoated with the last two coatings of example 5. The sample had good adhesion when tested according to Example 1 under wet and dry conditions, and the sample had good lubricity when wet.

EXAMPLE 15

A sample of stainless steel was dip coated with the following tie coat composition, and was dried for 2 hours at 85° C.

| | |
|---|---|
| Water | 8 gm |
| 10% Triton x 100 nonionic surfactant | .88 gm |
| 50% Acrylic dispersion polymer | 18.8 gm |

Next, the sample was overcoated with the last two coatings of example 5. The sample had good adhesion when tested according to example 1 under wet and dry conditions, and the sample had good lubricity when wet.

EXAMPLE 16

A sample of PEBAX polyamide tubing was treated according to Example 10. The sample had good adhesion when tested according to Example 1 under wet and dry conditions, and had good wet lubricity.

EXAMPLE 17

A sample of Nylon 12 tubing was treated as in Example 16, except that no oxygen plasma treatment was used. The sample had good adhesion when tested according to Example 1 under wet and dry conditions, and had good wet lubricity.

The embodiments illustrated and discussed in this specification are intended only to teach those skilled in the art the best way known to the inventors to make and use the invention. Nothing in this specification should be considered as limiting the scope of the present invention. Modifications and variations of the above-described embodiments of the invention are possible without departing from the invention, as appreciated by those skilled in the art in light of the above teachings. It is therefore to be understood that, within the scope of the claims and their equivalents, the invention may be practiced otherwise than as specifically described.

What is claimed is:

1. An insertable medical device comprising an abrasion resistant biocompatible surface coating applied to an inert surface of the device, the inert surface having no reactive functional groups, the surface coating comprising:
   (a) a coherent bond coat layer applied to the inert surface comprising at least one bonding polymer bonded with non-covalent bonds with the inert surface of the device without the need for penetration into the inert surface, and further comprising
   (b) at least one outer layer applied to the bond coat layer that adheres to the bond coat layer, the coating remaining adherent to the surface and resistant to abrasion and to removal from the device after soaking in water relative to a coating without the bond coat layer, and the coating remaining adherent when subjected to bending through a small radius.

2. A device according to claim 1, wherein the bonding polymer does not comprise chlorinated polyolefins.

3. A device according to claim 1, wherein the bonding polymer does not comprise a copolymer of a vinyl monomer and a carboxylic acid monomer.

4. A device according to claim 1, wherein the small radius has a diameter of less than about 3 cm.

5. A device according to claim 1, wherein the small radius has a diameter of less than about 1 cm.

6. A device according to claim 1, the inert surface having been pretreated with plasma or other ionizing pretreatment.

7. A device according to claim 6, said coating having been applied more than one day after the pretreatment.

8. A device according to claim 1, in which the bonding polymer is selected from the group consisting of acetals, ethylene copolymers, polymers containing hydroxyl, amine, carboxyl, or amide reactive groups, styrene acrylic polymer, ethylene acrylic acid copolymer, carboxyl function acrylic polymer, hydroxyl function acrylic polymer, acrylic dispersion polymers, methyl methacrylate, butyl methacrylate, isobutyl methacrylate, ethyl methacrylate, methyl acrylate, ethyl acrylate, acrylic acid, styrene methacrylate, and styrene acrylate, polyvinylpyrrolidone, vinylpyrrolidone-vinylacetate copolymers, ethylene acrylic acid copolymers, epoxy polymers, and copolymers thereof.

9. A device according to claim 1, wherein the bonding polymer includes reactive groups.

10. A device according to claim 9, the bond coat layer having been formed with a cross linker that interacts with reactive groups of the bonding polymer.

11. A device according to claim 10, wherein the cross linker is selected from the group consisting of urea resins, melamines, isocyanates, epoxies, and phenolics.

12. A device according to claim 1, wherein the bond coat layer has a thickness of less than about 100 microns.

13. A device according to claim 1, in which the bond coat thickness is between about 1 and about 10 microns.

14. A device according to claim 1, in which the surface coating has a total coating thickness of less than about 40 microns.

15. A device according to claim 1, in which the inert surface comprises a material selected from the group consisting of stainless steel, nickel, gold, chrome, nickel titanium alloy, platinum, metals, silicone, polyesters, polyolefins, polyethylene, polyprolylene, latex rubbers and polyisocyanates.

16. A device according to claim 1 selected from the group consisting of needles, guide wires, catheters, surgical instruments, equipment for endoscopy, wires, stents, angioplasty balloons, wound drains, arteriovenuous shunts, gastroenteric tubes, urethral inserts, laproscopic equipment, pellets, and implants.

17. A device according to claim 1, wherein the outer layer comprises at least one of a lubricious coating, a medicated coating, a colored coating and an abrasion resistant coating.

18. A device according to claim 1, further comprising covalent bonds between the bond coat layer and the surface of the device.

19. A device according to claim 1, wherein the coating is resistant to removal by adhesive tape after soaking.

20. A device according to claim 1, wherein the coating is applied without subjecting the coating to heating for more than about six hours.

21. A device according to claim 1, wherein the outer layer is hydrophilic and the bond coat layer resists penetration of water to the surface of the device.

22. A device according to claim 1, prepared by a method comprising the steps of forming the bond coat layer and then forming the coating layer over the preformed bond coat layer.

23. A composition adapted for forming a biocompatible surface coating on an inert surface of a medical device, the composition comprising a biocompatible bonding polymer that bonds non-covalently with the inert surface of the device without the need for penetration into the inert surface to form a bond coat, the bonding polymer further being selected to adhere to an outer layer applied over the bond coat layer, the coating remaining adherent to the substrate and resistant to abrasion and removal by adhesive tape after soaking in water and the coating remaining adherent when subjected to bending through a small radius.

24. A composition according to claim 23, wherein the bonding polymer does not comprise a chlorinated polyolefin.

25. A composition according to claim 23, wherein the bonding polymer is not a copolymer of a vinyl monomer with a carboxylic acid monomer.

26. In a biocompatible coating comprising an outer layer on an insertable medical device having an inert surface without reactive functional groups, the improvement comprising a coherent bond coat layer formed by a bonding polymer that bonds non-covalently with the inert surface of the device without the need for penetration into the inert surface, the bonding polymer further adhering to an outer layer applied over the bond coat layer, the coating remaining adherent to the substrate and resistant to abrasion and removal during a period of insertion relative to a coating without the bond coat and the coating remaining adherent when subjected to bending through a small radius of about 3 cm.

27. An abrasion-resistant coating applied to an insertable medical device comprising an inert surface that does not have reactive functional groups, the coating comprising:

(a) a coherent bond coat layer applied to the inert surface comprising at least one bonding polymer bonded with non-covalent bonds with the inert surface of the device without the need for penetration into the device, and further comprising (b) at least one outer layer applied to the bond coat layer that adheres to the bond coat layer, the coating remaining adherent to the surface and resistant to abrasion and to removal from the device after soaking in water relative to a coating without the bond coat layer, and the coating remaining adherent when subjected to bending through a small radius.

* * * * *